United States Patent
Magovern et al.

[19]

[11] Patent Number: 6,106,550

[45] Date of Patent: Aug. 22, 2000

[54] IMPLANTABLE ATTACHING RING

[75] Inventors: James A. Magovern, Pittsburgh, Pa.; Louis A. Campbell, Austin, Tex.

[73] Assignee: Sulzer Carbomedics Inc., Austin, Tex.

[21] Appl. No.: 09/114,008

[22] Filed: Jul. 10, 1998

[51] Int. Cl.[7] .................................................... A61F 2/24
[52] U.S. Cl. ................................................... 623/2.38
[58] Field of Search .................................. 623/2, 3, 2.11, 623/2.38, 2.39, 2.4

[56] References Cited

U.S. PATENT DOCUMENTS

| | | | |
|---|---|---|---|
| 3,143,742 | 8/1964 | Cromie | 623/2 |
| 3,371,352 | 3/1968 | Siposs et al. | 3/1 |
| 3,409,013 | 11/1968 | Berry | 128/303 |
| 3,445,916 | 5/1969 | Schulte | 29/458 |
| 3,464,065 | 9/1969 | Cromie | 3/1 |
| 3,524,202 | 8/1970 | Cromie | 3/1 |
| 3,587,115 | 6/1971 | Shiley | 623/2 |
| 3,725,961 | 4/1973 | Magovern et al. | 3/1 |
| 4,612,011 | 9/1986 | Kautzky | 623/2 |
| 4,680,031 | 7/1987 | Alonso | 623/2 |
| 4,687,483 | 8/1987 | Fisher et al. | 623/2 |
| 4,892,541 | 1/1990 | Alonso | 623/2 |
| 5,071,431 | 12/1991 | Sauter et al. | 623/2 |
| 5,522,884 | 6/1996 | Wright | 623/2 |
| 5,855,603 | 1/1999 | Reif | 623/2 |
| 5,891,195 | 4/1999 | Klostermeyer et al. | 623/2 |

*Primary Examiner*—David H. Willse
*Assistant Examiner*—Suzette J. Jackson
*Attorney, Agent, or Firm*—Timothy L. Scott; Philip S. Lyren; Kenneth S. Barrow

[57] ABSTRACT

An implantable attaching device includes an annular ring having an axial passageway and a plurality of channels extending radially through the ring. Tissue attaching pins are positioned in the channels and extend radially inward into the axial passageway during implantation. The pins are driven into the native annulus tissue after the ring is positioned. Once the pins are driven into the annulus, the axial passageway of the ring is unobstructed and is adapted to receive a heart valve or other implantable device.

18 Claims, 3 Drawing Sheets

IMPLANTABLE ATTACHING RING

BACKGROUND OF THE INVENTION

The present invention relates to an implantable device for receiving a heart valve or other implantable device.

Implantable heart valves are used to replace a diseased or otherwise damaged native heart valve in order to restore the heart to ordinary function. Typically, the valve is implanted in the annulus where the damaged valve was removed. Generally, there are two types of implantable heart valves: 1) "mechanical" valves; and 2) "tissue" valves. A mechanical valve includes pyrolitic carbon, metal or plastic surfaces which rotate or are otherwise displaced to regulate blood flow. A tissue valve includes all or part of a heart valve from a non-human, e.g., a porcine animal, a human valve transplant called a homograft, a valve constructed from animal tissue other than valve tissue, e.g. pericardial valves or transposition of a valve from one site to another site in the same person called an autograft to regulate blood flow. With both types of valves, a generally annular structure is frequently used to position and support the valve in the native annulus. An important goal of heart valve design is to minimize the obstruction of blood flowing through the native annulus.

In a common implantation procedure, the implantable heart valve is sewn into the native annulus, fixing the valve in place until native tissue growth around the valve provides a permanent attachment, see e.g., U.S. Pat. No. 3, 524,202. This implantation procedure is time consuming and requires good visual access to the native valve, as well as access for needles, needle holders, a valve seating device, and the surgeon's hands. This procedure requires cardiopulmonary bypass (CPB) and myocardial preservation measures to arrest the heart for an extended period. There measures have improved since early valve implantation procedures. Additionally, the current trend in surgery is toward less invasive surgical techniques.

One approach for reducing the implantation time is the use of "sutureless" heart valves, see e.g., U.S. Pat. Nos. 3,587,115, 3,464,065, 3,371,352, and 3,143,742. Such sutureless designs typically include pins positioned about the annular valve support structure. When the valve is positioned in the native annulus, a mechanism is used to drive the pins into the surrounding annulus tissue, thereby holding the valve in place until native tissue growth provides a permanent attachment. One limitation of these sutureless designs is that the pre-positioned pins and the driving mechanism increase the radial width of the valve support structure, thereby decreasing the size of the blood flow passage through the valve.

Another implantation approach incorporates a two-part valve assembly, see e.g., U.S. Pat. Nos. 4,892,541 and 4,680,031. The first part of the assembly is a sewing ring, which is positioned and manually sewn into the annulus as described above. The valve comprises the second part, and is removably coupled with the sewing ring. This approach provides for faster removal of a failed valve, but has the limitations described above for sewing the ring into the annulus.

SUMMARY OF THE INVENTION

The present invention is directed to an implantable device for receiving a heart valve or other implantable device. The device includes an annular ring which defines an axial passageway. The radial thickness of the ring is minimized. A plurality of radial channels extend through the ring and are spaced circumferentially about the ring. A pin is positioned with respect to each channel so that a first end of the pin is positioned in a channel and a second end extends into the axial passageway. Once the ring is positioned in the native annulus, the pins are driven into the annulus tissue, securing the ring in place and clearing the axial passageway to receive a heart valve.

Consequently, an attaching ring is provided which may be rapidly inserted and attached to the annulus. Also, once the pins are driven into the annulus tissue, the attaching ring provides a maximized axial passageway for receiving a heart valve. This configuration allows for a maximized blood flow passage through the heart valve, and also minimizes areas where blood may stagnate, reducing the possibility of thrombosis. Additionally, the surgeon can work in a smaller space, because the ring is implanted without the need for traditional suturing techniques.

The ring and pins are comprised of biocompatible, non-toxic, non-thrombogenic materials. In one embodiment, the ring comprises titanium metal or other relatively rigid, biocompatible material. The pins comprise a shape-memory or super-elastic material, such as a nickel titanium alloy. The pins are positioned in the ring channels by a frictional fit or are held in place by a separate tool. Shaped-memory or super-elastic materials allow the pins to bend into desired configurations upon implantation, providing an improved attachment to the surrounding annulus tissue, as opposed to extending pins (radially) straight into the tissue.

In one embodiment, the ring also comprises a lip extending radially outward from an upper portion if the ring. The lip assists in seating the ring in the annulus and provides a seal between the ring and annulus. Also, the lower portion of the lip provides a surface into which curved pins may be driven, providing an improved attachment. The radially outward surface of the ring may comprise a fabric or porous metal or plastic which promotes tissue growth from the native annulus, providing a long-term, secure attachment.

In one embodiment, an implantable heart valve (mechanical or tissue) is removably coupled with the attaching ring. This connection further reduces implantation time. In another embodiment, the attaching ring is adapted to receive other implantable devices, e.g., vascular grafts.

Other advantages and features will become apparent from the following description and claims.

DETAILED DESCRIPTION OF THE EMBODIMENTS

Figure 1:
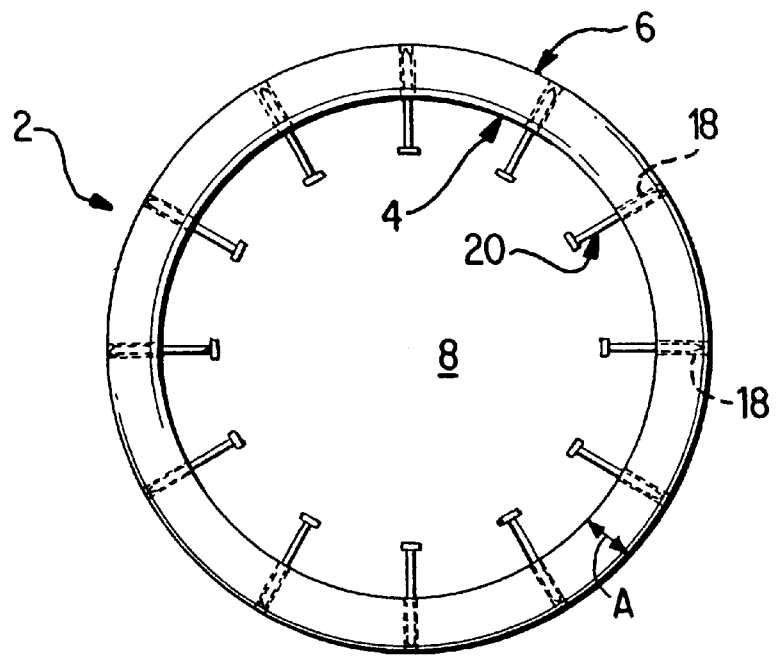
FIG. 1 is a plan view of an attaching ring with pins positioned for implantation.

An attaching ring according to the invention is shown in FIG. 1. Ring 2 comprises a generally annular structure having an inner wall 4 and an outer wall 6. Inner wall 4 defines an axial passageway 8. The radial width or thickness of ring 2 (as shown by dimension A) is minimized in order to maximize the cross-sectional area of axial passageway 8 for a given outer wall 6 diameter. The diameter of outer wall 6 is selected so that ring 2 will fit securely within the native annulus.

Ring 2 comprises a biocompatible, non-toxic, non-thrombogenic material. In one embodiment, ring 2 is made from titanium. The radial width (A) of a titanium ring ranges between 70/1000 inch and 7/1000 inch. Of course, other relatively rigid, biocompatible materials may be used, and manufacturing improvements may allow a smaller radial width.

Figure 2:
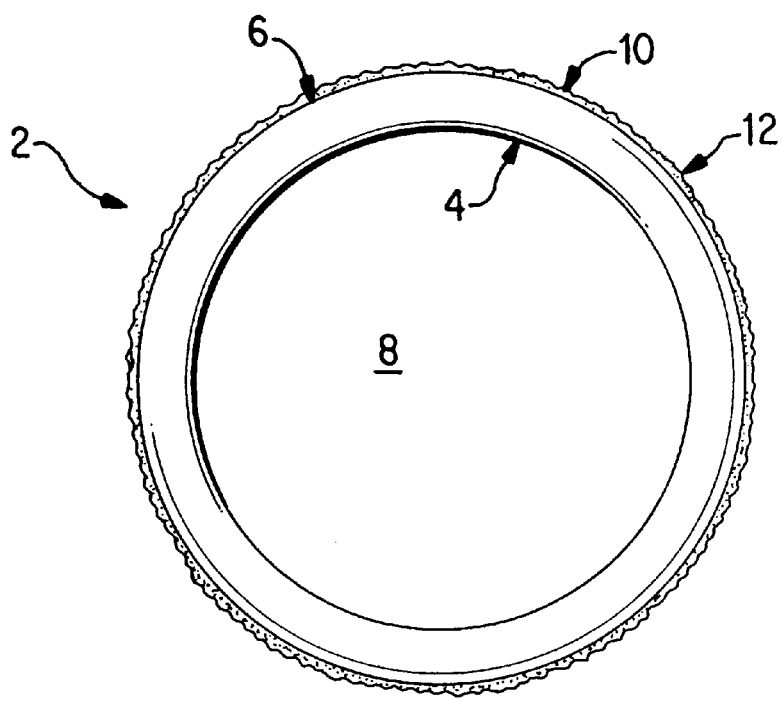
FIG. 2 is a plan view of an attaching ring with a fabric band.

As shown in the embodiment of FIG. 2, a fabric band or cuff 10 is positioned radially outward from outer wall 6 of ring 2. Fabric band 10 comprises a polyester cloth or other porous biocompatible material. Fabric band 10 provides an irregular surface 12 which promotes tissue growth from the surrounding annulus tissue onto ring 2. This tissue growth provides a long-term, secure attachment between ring 2 and the native annulus. In another embodiment (not shown), outer wall 6 may be an irregular surface or be coated with a material having an irregular surface, again promoting tissue growth.

Figure 3:
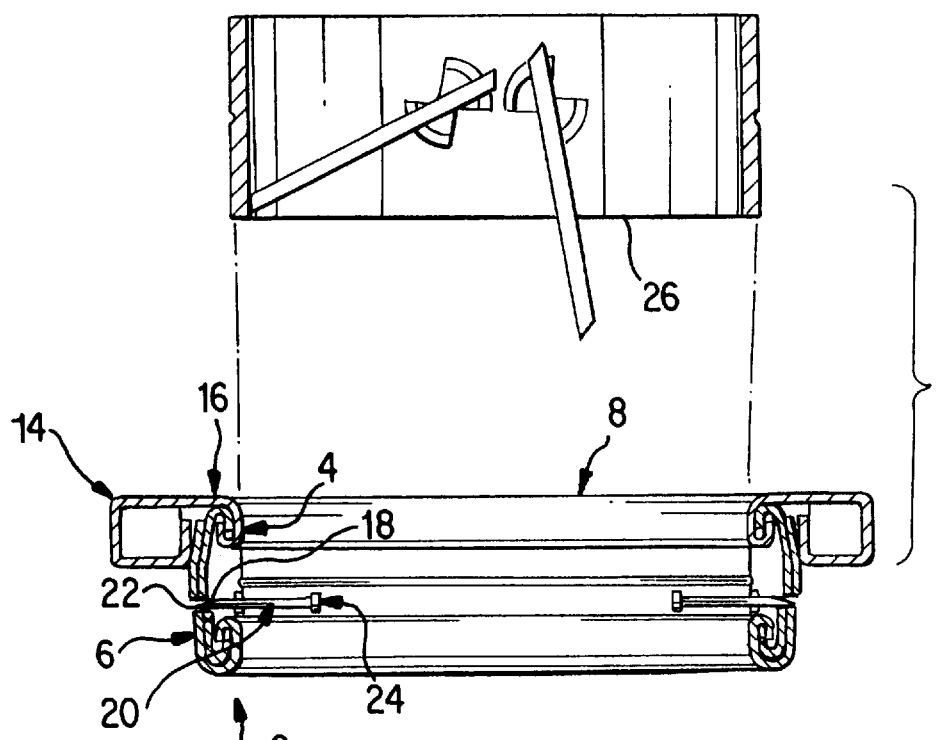
FIG. 3 is a partial cut-away and exploded view of an attaching ring and heart valve with the engaging pins retracted prior to tissue engagement.

In the embodiment shown in FIG. 3, ring 2 includes a lip 14 extending radially outward from outer wall 6 at a first end 16 of ring 2. Lip 14 assists the surgeon in seating ring 2 in the native annulus and also assists in forming a seal between ring 2 and the native annulus.

Figure 4:
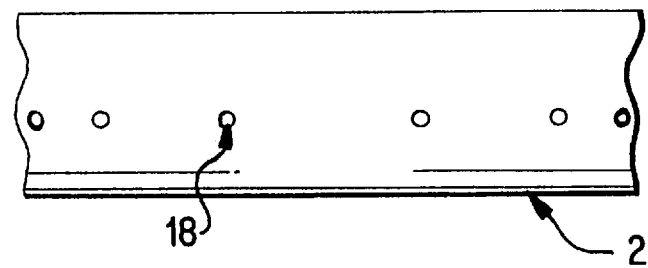
FIG. 4 is a partial side view of an attaching ring.
Figure 5:
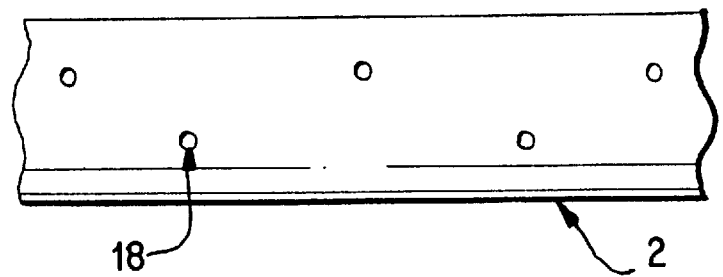
FIG. 5 is a partial side view of another embodiment of an attaching ring.

As shown in FIG. 1, a plurality of passages or channels 18 extend through ring 2, i.e., they extend radially outward from inner wall 4 to outer wall 6. The passages are spaced circumferentially about ring 2. In the embodiment shown in FIG. 4, the channels are generally coplanar. In another embodiment, the channels are staggered, as shown in FIG. 5. At least three channels are provided so that three pins inserted into the native annulus provide minimum stability for ring 2. In one embodiment, there may be as many as twenty channels 18.

As shown in FIG. 1, a tissue attachment pin 20 is positioned in a channel 18. As shown in FIG. 3, each pin 20 has a first or piercing end 22. While moving ring 2 into position in the native annulus, first end 22 of each pin 20 is positioned in its respective channel 18, i.e., the first end 22 of each pin 20 does not extend beyond outer wall 6. Therefore, ring 2 may be positioned in the native annulus without the risk of the first ends 22 damaging the annulus tissue.

Each pin 20 also includes a second or driving end 24, FIG. 3, extending radially inward from first end 22. During implantation, second end 24 extends into axial passageway 8. Once ring 2 is suitably positioned, pins 20 are driven into the annulus tissue by applying a force to second ends 24. Consequently, axial passageway 8 is unobstructed, providing a maximum cross-sectional area for receiving a heart valve 26, as shown in FIG. 6.

Pins 20 comprise biocompatible, non-toxic, non-thrombogenic materials. In one embodiment, pins 20 comprise a super-elastic or shape-memory material, such as nickel titanium alloy. Therefore, pins 20 have a first shape, e.g., linear, when constrained by the channel and the instrument used to engage the pins, and a second curved shaped that will optimally engage the annulus tissue. In the embodiment shown in FIG. 6, pins 20 curve into a lower surface 28 of lip 14, providing a secure attachment with the annulus tissue. As shown in FIG. 6, pins 20 have a shape memory, so that upon implantation, pins 20 are driven into the annulus tissue and curve back into surface 28.

In one embodiment, a pin 20 is held in channel 18 by frictional forces, i.e., the diameter of pin 20 is about the same as the channel diameter. During implantation, the driving force on the second end 24 of pin 20 overcomes the fictional forces and the first end 22 of pin 20 extends radially outward into the annulus tissue. Typically, several pins are used to anchor the valve but at least three pins are used to provide minimum stability for ring 2 seated in the annulus. In another embodiment (not shown), a tool is used to grasp the second ends 24 of pins 20, thereby hold pins 20 in place during implantation. When pins 20 are to be driven into the annulus tissue, the tool releases the second ends 24.

Figure 6:
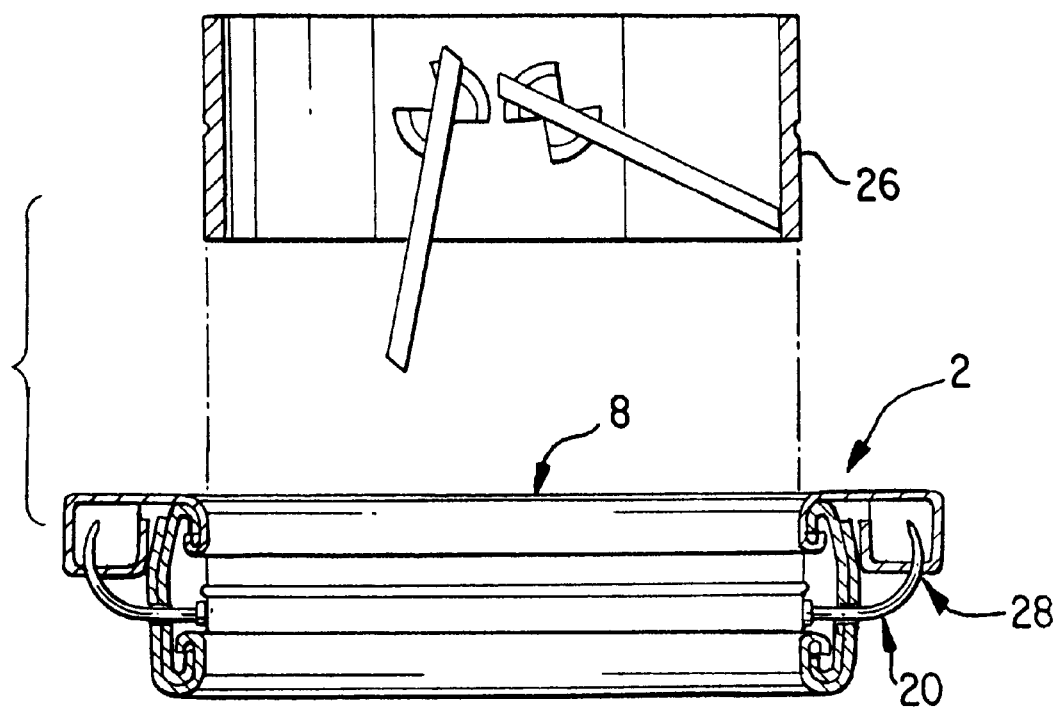
FIG. 6 is a partial cut-away and exploded view of an attaching ring and heart valve with the engaging pins extended for tissue attachment.

As shown in the embodiment of FIG. 6, ring 2 is adapted to receive heart valve 26. Heart valve 26 comprises a mechanical or tissue valve. In one embodiment, valve 26 may be removably coupled with ring 2 by a snap fit, as disclosed in U.S. Pat. No. 5,071,431, incorporated herein by reference. In another embodiment, a threaded coupling may be used, as disclosed in U.S. Pat. No. 4,892,541, incorporated herein by reference. Other coupling mechanisms may also be used. Ring 2 is adaptable for use in any type of heart valve implantation, i.e., mitral, aortic, pulmonary or tricuspid valve implantation. In another embodiment, ring 2 may be adapted to receive a vascular graft or other implantable device.

Other embodiments are within the scope of the following claims.

We claim the following:

1. An implantable apparatus for receiving a heart valve, comprising:

an annular ring having an inner wall and an outer wall, the inner wall defining an axial passageway;

a plurality of channels displaced circumferentially about the ring, each channel extending from the inner wall to the outer wall; and a plurality of tissue attachment pins each pin being movable in a respective one of the channels between a first position, wherein a first end of each pin is positioned in its respective channel adjacent the outer wall and a second end of each pin extends into the axial passageway during implantation, and a second position wherein the first end of each pin extends beyond the outer wall for tissue attachment, and the second end of each pin is moved toward the channel and out of the axial passageway.

2. The apparatus of claim 1 further comprising a lip extending radially outward from a first end of the annular ring.

3. The apparatus of claim 1 further comprising a fabric band extending radially outward from the annular ring.

4. The apparatus of claim 1 further comprising means for selectively coupling a heart valve with the annular ring.

5. An implantable device, comprising:

an annular body defining an axial passageway therethrough;

a plurality of circumferentially-spaced radial passages;

a plurality of selectively movable tissue attachment needles;

means for retaining the fixation needles in respective passages during implantation, a first end of each needle being positioned in a passage and a second end extending into the axial passageway;

a seating lip extending radially outward from the annular body; and a cuff extending radially outward from the annular body.

6. The apparatus of claim 5 further comprising means for selectively coupling a second implantable device with the annular body.

7. An implantable heart valve assembly, comprising:

an annular attaching member having an interior wall and exterior wall, the interior wall defining a heart valve receiving passage;

a plurality of circumferentially-spaced apertures, each aperture extending from the interior wall to the exterior wall;

a plurality of piercing elements, a first end of each piercing element being extendibly constrained in its respective aperture between the interior and exterior walls, and a second end of each piercing element extending into the valve receiving passage during implantation; and each piercing element having a first linear shape when constrained in its respective aperture and a second curved shape when extended from the aperture.

8. The heart valve assembly of claim 7 further comprising a heart valve selectively coupled with the annular attaching member.

9. The heart valve assembly of claim 7 further comprising a lip extending radially outward from the annular attaching member.

10. The heart valve assembly of claim 7 further comprising a fabric band extending radially outward from the annular attaching member.

11. The heart valve assembly of claim 7 wherein the piercing elements are formed of a super-elastic material.

12. The heart valve assembly of claim 7 wherein the piercing elements are formed of a shape-memory material.

13. The heart valve assembly of claim 9 wherein the first end of the piercing element engages the lip when extended from the aperture.

14. The heart valve assembly of claim 7 wherein the apertures are radially disposed within the annular attaching member.

15. The heart valve assembly of claim 7 wherein the apertures are coplanar.

16. The heart valve assembly of claim 7 wherein the apertures are staggered.

17. The heart valve assembly of claim 7 wherein there are at least three apertures.

18. The heart valve assembly of claim 7 wherein the piercing elements are frictionally constrained in the apertures.

* * * * *